(12) United States Patent
Puah et al.

(10) Patent No.: US 7,573,569 B2
(45) Date of Patent: Aug. 11, 2009

(54) SYSTEM FOR 2-D AND 3-D VISION INSPECTION

(75) Inventors: Yong Joo Puah, Singapore (SG); Hak Wee Tang, Seletaris (SG); Fan Hua, Singapore (SG)

(73) Assignee: Generic Power Pte Ltd, Singapore (SG)

( * ) Notice: Subject to any disclaimer, the term of this patent is extended or adjusted under 35 U.S.C. 154(b) by 389 days.

(21) Appl. No.: 11/573,344

(22) PCT Filed: Sep. 1, 2005

(86) PCT No.: PCT/SG2005/000301

§ 371 (c)(1),
(2), (4) Date: Feb. 6, 2007

(87) PCT Pub. No.: WO2006/038885

PCT Pub. Date: Apr. 13, 2006

(65) Prior Publication Data

US 2007/0247614 A1    Oct. 25, 2007

(30) Foreign Application Priority Data

Oct. 6, 2004    (SG) .............................. 200405729-5

(51) Int. Cl.
*G01N 21/00* (2006.01)
*G01B 11/24* (2006.01)

(52) U.S. Cl. .................................. 356/237.2; 356/601

(58) Field of Classification Search ....................... None
See application file for complete search history.

(56) References Cited

U.S. PATENT DOCUMENTS

2002/0030808 A1*    3/2002    Bostrom et al. .......... 356/237.2
2007/0103675 A1*    5/2007    Vodanovic ............... 356/237.1

* cited by examiner

*Primary Examiner*—Gregory J Toatley, Jr.
*Assistant Examiner*—Amanda H Merlino
(74) *Attorney, Agent, or Firm*—Lawrence Y D Ho & Associates Pte. Ltd.

(57) ABSTRACT

There is disclosed an inspection system that combines 2-D inspection and 3-D inspection of the components of an electronic device into one compact module. The inspection system of the present invention comprises a 2-D image acquisition assembly for inspecting 2-D criteria of the components, a 3-D image acquisition assembly for inspecting 3-D criteria of the components, and a computer for control and data analyzing. The 3-D image acquisition assembly comprises a 3-D image sensor and a 3-D light source. The 3-D light source is preferably a laser capable of generating a planar sheet of light that is substantially perpendicular to the inspection plane of the electronic device. The 2-D image acquisition assembly comprises a 2-D sensor and a 2-D light source positioned above the holder. The 2D and 3D image acquisition assemblies are arranged so that the 2D inspection and 3D inspection can be done while the electronic device is being held in one location.

12 Claims, 5 Drawing Sheets

SYSTEM FOR 2-D AND 3-D VISION INSPECTION

FIELD OF THE INVENTION

The present invention relates generally to an inspection system that performs three dimensional (3-D) and two dimensional (2-D) criteria analysis. More specifically, the 3-D and 2-D criteria analysis is used to perform inspection of integrated circuit (IC) devices.

BACKGROUND OF THE INVENTION

There is a need in the manufacturing of IC devices for inspection of electronic components such as leads and solder balls of semiconductor packages. Several systems are available for separate 2-D and 3-D inspection of semiconductor packages.

U.S. Pat. No. 5,956,134 discloses a lead inspection system that is operable to make both 2-D and 3-D measurements of semiconductor packages while there are relative movement between the lead inspection system and the semiconductor packages. This system includes a first optical sensor, e.g. a CCD camera, oriented to capture a 2-D image of a semiconductor device package and compare the image with a predetermined 2-D image stored in a central processing unit (CPU). A high intensity light source, such as a laser, generates a plane of light which is reflected off the leads of the semiconductor package to a second optical sensor, e.g. another CCD camera, wherein a 3-D image is generated. The CPU compares the 3-D image with the predetermined or calculated positional relationships of the leads to establish co-planarity of the lead tips, or lack thereof. This system also includes a sensor located such that the semiconductor package is centered in a field of view of the cameras to capture the respective images. The disadvantages of '134' are that it has different centers in field of view for 2-D and 3-D respectively, and requires a separate mechanism to pick up and orientate the targeted device before inspection can be performed.

U.S. Pat. No. 6,118,540 discloses an inspection system for automatically inspecting 2-D and 3-D criteria of packaged semiconductor devices using a single camera and several laser sources. A 2-D lighting is provided to illuminate the object under inspection. A single camera captures the image of the object. This provides the image data for 2-D analysis by a computer coupled to the system. Multiple laser sources provide the illumination for performing 3-D criteria measurements. One disadvantage of this system is that one camera are used for both 2D and 3D inspection, which will slow down the inspection throughput. The disparity in the amount of data input from 2-D and 3-D criteria becomes a bottleneck for the inspection speed of the inspection system that uses only one camera.

U.S. Pat. No. 6,291,816 discloses an imaging system that utilizes both 2-D and 3-D scanning assemblies. The 2-D scanning assembly pre-scans a selected region of an object. The data from the 2-D scanning assembly is used to predetermine areas containing 3-D features of interest and to direct the 3-D scanning assembly. The 2-D scanning assembly includes a line camera or an area array camera. The 3-D scanning assembly includes a laser for 3-D illumination, an acoustic optical (AO) deflector and a position sensitive device (PSD) detector. This system is complicated and expensive to set up.

There remains a need for an inspection system that is relatively simple, compact and inexpensive to set up while improving the speed of 3D inspection.

SUMMARY OF THE INVENTION

The present invention is directed to an inspection system that combines 2-D inspection and 3-D inspection of the components of an electronic device into one compact module. The inspection system of the present invention comprises, a 2-D image acquisition assembly for inspecting 2-D criteria of the components, a 3-D image acquisition assembly for inspecting 3-D criteria of the components, and a processing unit connected to the 2-D image acquisition assembly and the 3-D image acquisition assembly for analyzing the 2-D and the 3-D images. The 3-D image acquisition assembly comprises a 3-D image sensor and a 3-D light source. The 3-D light source is preferably a laser capable of generating a planar sheet of light that is substantially perpendicular to the plane of the electronic device. The 2-D image acquisition assembly comprises a 2-D sensor and a 2-D light source positioned above the holder. The 2-D and 3-D image acquisition assemblies are arranged so that the 2-D inspection and 3-D inspection can be done while the electronic device is being held in one location.

The present invention combines 2-D and 3-D inspection function into one module with a beam splitter. 2-D and 3-D systems are aligned so that they have the same center in field of view. Different cameras are utilized because of different requirements and selection criteria. The 2-D camera is a normal camera, typically is a CCD camera. It concentrates on 2-D feature inspection such as the location and dimension of ball/lead and defects on the device surface etc. The 3-D camera is a high speed CMOS sensor camera with programmable window size working together with a high-speed data process hardware unit.

BRIEF DESCRIPTION OF THE DRAWINGS

The advantages and novel features of the present invention will become apparent from the following detailed description of exemplary embodiments taken in conjunction with the attached drawings.

DETAILED DESCRIPTION OF THE EMBODIMENTS

Figure 1:
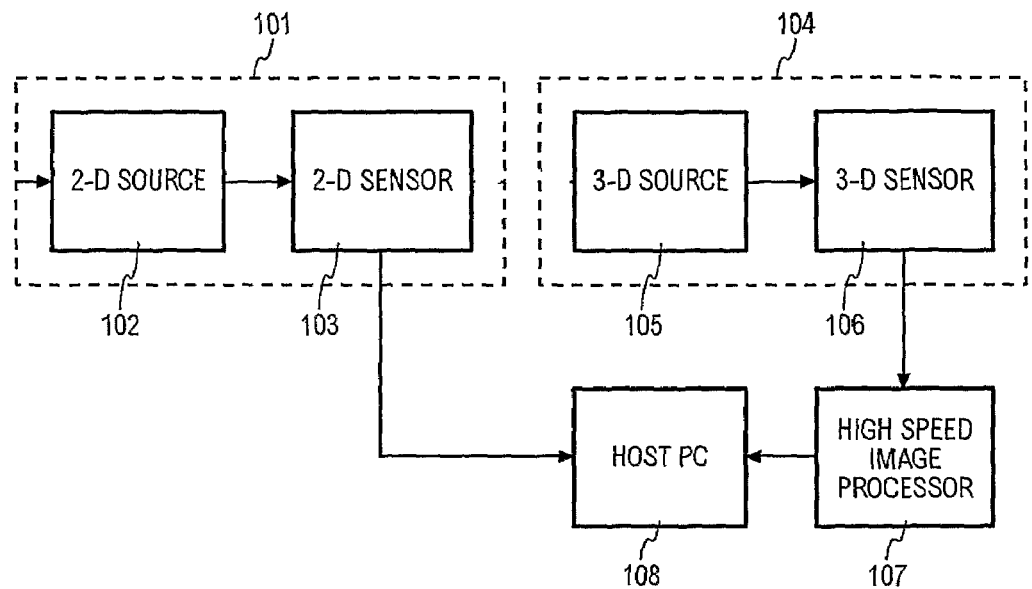
FIG. 1 shows a schematic block diagram representing the basic arrangement of the inspection system according to the preferred embodiment of the present invention.

FIG. 1 shows a schematic block diagram representing the basic arrangement of the inspection system according to the preferred embodiment of the present invention. The inspection system of the present invention comprises four basic components: a 2-D image acquisition assembly 101, which includes a 2-D light source 102 and a 2-D sensor 103; a 3-D image acquisition assembly 104, which includes a 3-D light source 105 and one or two 3-D sensor 106; a host programmable computer (PC) 108; and a high speed image processor 107. The 2-D light source 101 illuminates an electronic device to be inspected, e.g. an IC package. The 2-D image of the components of the electronic device is then captured by the 2-D sensor 102. The 2-D image is sent to host 108 for performing 2 dimensional images processing tasks. At the same time, the 3D light source 105 is activated to illuminate the device while it is being held in the same location. The 3-D image of the components is captured by the 3-D sensor 106. The raw image from the sensor 106 is sent to the high-speed image processor 107 for reformatting the image data and extracting the laser centerline in real time. The extracted laser line by the image processor 107 is fetched by the host 108 to calculate the 3-D parameters such as, sold ball height, co-planarity and warpage etc. The host 108 computes the 2-D and 3-D inspection results to determine whether to reject or accept the device with reference to predetermined specifications.

Figure 2:
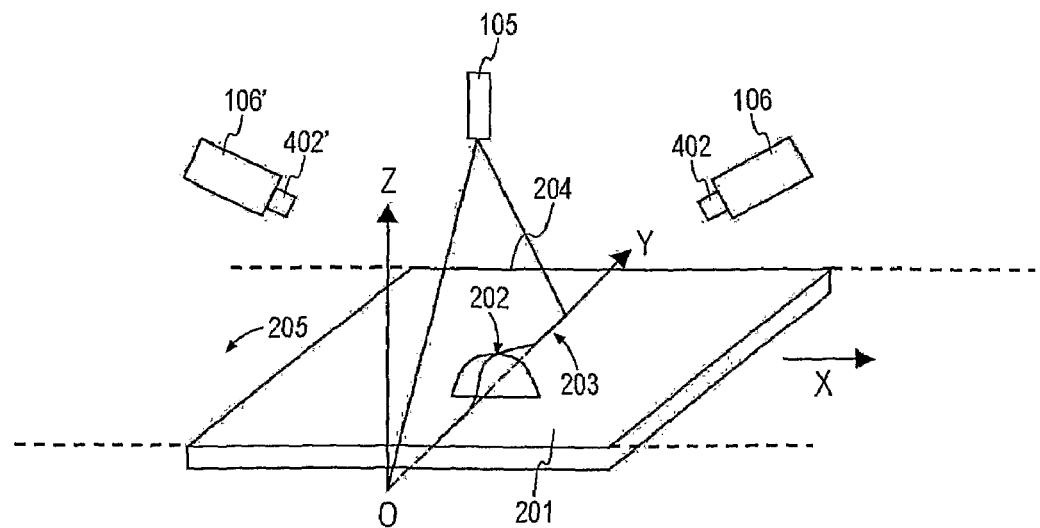
FIG. 2 shows a configuration of the 3-D image acquisition assembly according to the preferred embodiment of the present invention.

FIG. 2 shows the configuration of the 3-D image acquisition assembly 104 according to the preferred embodiment of the present invention. The details of the 2-D image acquisition assembly 101 is omitted in FIG. 2 and will be described subsequently with reference to FIGS. 4 and 5. Referring to FIG. 2, an electronic device 201 is positioned in an inspection plane 205 and is supported by a conventional holder (not shown). The device 201 contains components 202 to be inspected, e.g. solder ball lead (only one solder ball is shown herein). During inspection, the device 201 and 3-D sensor constructed by comprise of camera 106, 106' and laser 105 have to move relatively. FIG. 2 only shows the device moving along direction X. Another possibility is the 3-D sensor is moving while the device is standstill. A 3-D camera 106 is mounted above the inspection plane 205 at an acute angle, for example, 45°, relative to the inspection plane 205. A 3-D light source 105, preferably a diode laser, is mounted above the inspection plane 205 and is capable of generating a planar sheet of light 204 onto the device 201. The 3-D light source 105 is positioned so that the sheet of light 204 is substantially perpendicular to the inspection plane 205 as shown in FIG. 2. In order to increase the inspection speed and reduce the shadow effect caused by the height of the component 202, a second 3-D image sensor 106' is provided. In addition, the second 3-D sensor 106' is also capable of inspecting the blind spot of the first 3-D sensor 106. The second 3-D sensor 106' is mounted symmetrically relative to the first 3-D camera 106. The 3-D camera 106 and 106' may be high-speed cameras with lens 402 and 402', respectively. In operation, the 3-D light source 105 provides lighting on the device 201 and the random reflection light from the surface of device 201 is imaged through lens 402 and 402' and received by 3-D cameras 106 and 106'. The 3-D cameras 106 and 106' are operable to convert the distortion of the deformed laser line 203 into digital image.

Figure 3:
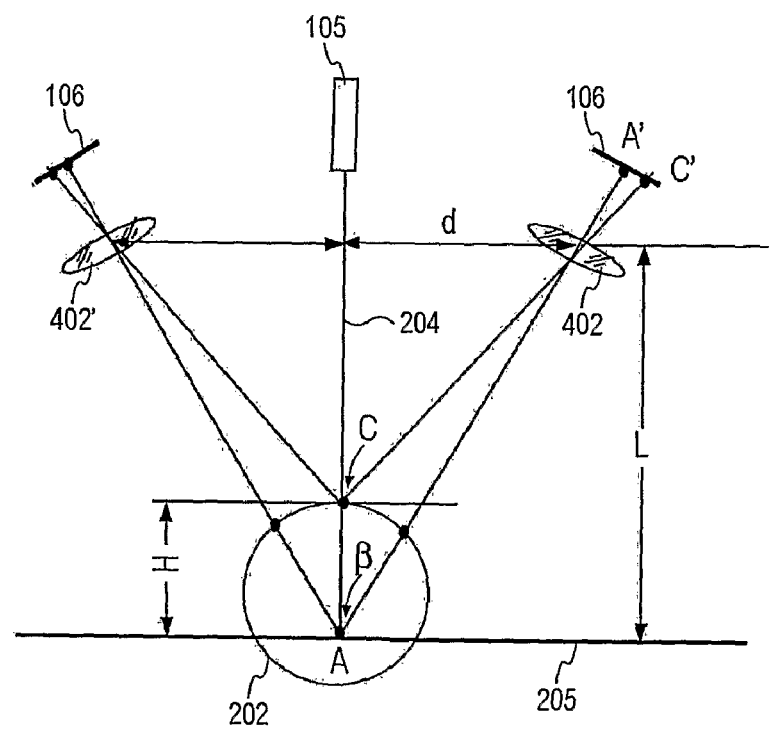
FIG. 3 illustrates a 3-D data analysis.

FIG. 3 illustrates how the ball height is calculated from the deformed laser line 203. The solder ball 202 is viewed by lens 402 at an oblique angle β and is imaged on the inspection plane 205, assuming that the solder ball 202 is within the depth of focus of the camera 106. The solder ball has a top point C, a bottom point A and a height H, which is equal to the distance between the top point C and the inspection plane 205. When the sheet of light 204 hits the solder ball 202, the straight laser line 203 become deformed. The relationship between the distortion $\overline{A'C'}$ of the laser line and the distance H can be determined as follows:

$$H = \frac{L}{Md} \cdot \overline{A'C'}$$

Where M is the magnification of the lens, L is the distance between the optical center of lens 402 and the inspection plane 205, and d is the distance between the optical center of lens 402 and the sheet of light 204. L and d are system parameters that have to be calibrated. The above relation is based on the assumption that L>>H so that H is negligible relative to L. The distortion $\overline{A'C'}$ can be obtained on the imaging plane of an image sensor. Similar calculations can be done using the second 3-D camera 106' and lens 402'.

Figure 4:
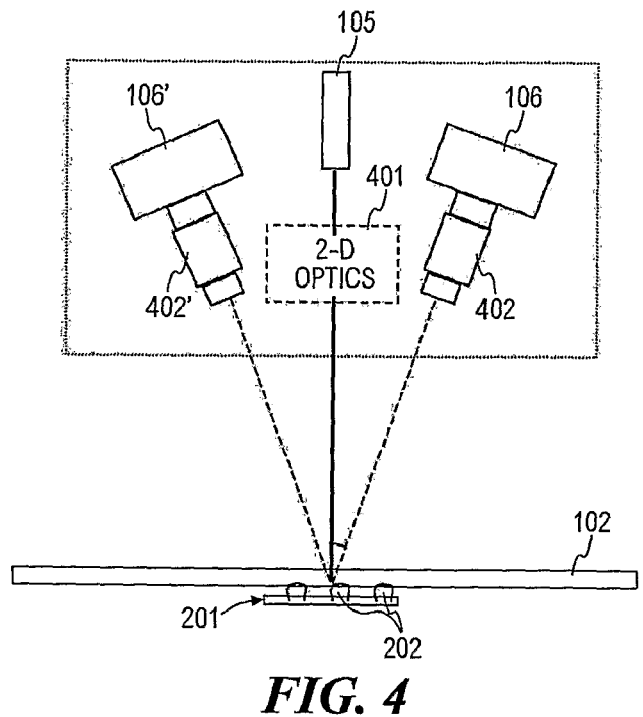
FIG. 4 shows a front view of the inspection system of the present invention.

FIG. 4 shows a front view of the inspection system of the present invention. The configuration of the 3D image acquisition assembly with two cameras 106 and 106' is as described for FIG. 2. As shown in FIG. 4, the 2-D light source 102 is mounted above the device 201, but below the 3-D light source laser 105, and a 2-D optics 401 is provided for diverting the device image and enabling the integration of this 2-D acquisition assembly with 3-D acquisition assembly. The 2-D light source may be a ring-shaped light emitting diode (LED) array.

Figure 5:
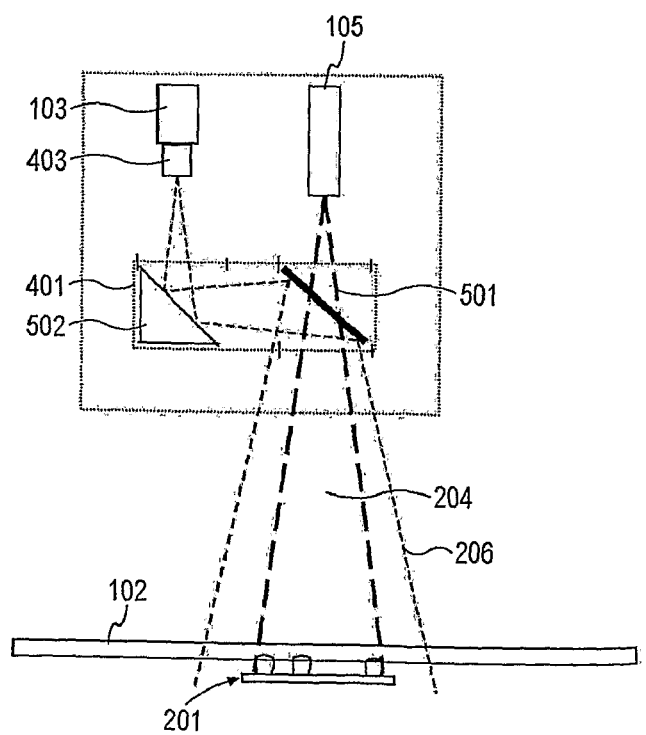
FIG. 5 shows the optics to combine 2-D image system with 3-D lighting.

Referring to FIG. 5, the 2-D sensor 103 is a camera provided with a lens 403. The 2-D sensor 103 may be a normal speed 2-D camera such as a charge coupled device (CCD) or a CMOS-based camera. The 2-D optics 401 includes a beam splitter 501 with transmission against reflect ratio of 50:50 and a mirror 502 for changing the direction of the optics. As shown in FIG. 5, the laser 105 and the 2-D light source 102 are co-axially aligned. In 2-D operation, the 2-D light source 102 illuminates the device. The filed of view (shown by the dash line 206) must be designed to cover the biggest device to be inspected.

Referring again to FIG. 5, it should be noted that the 2-D inspection acquisition assembly 101 and the 3-D inspection acquisition assembly 103 can work independently from each other. It follows that the 2-D optics 401 and 2-D imaging sensor (103 and 403) may be removed when only the 3-D inspection acquisition assembly is required.

Figure 6:
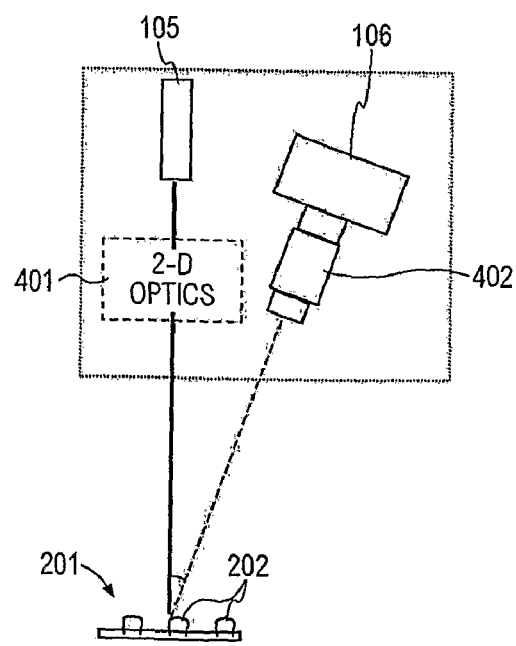
FIG. 6 shows an alternative configuration for the 3-D image acquisition assembly, in which only one 3-D camera is used.

FIG. 6 shows an alternative configuration for the 3-D image acquisition assembly 104. In this embodiment, only one camera 106 is provided.

Figure 7:
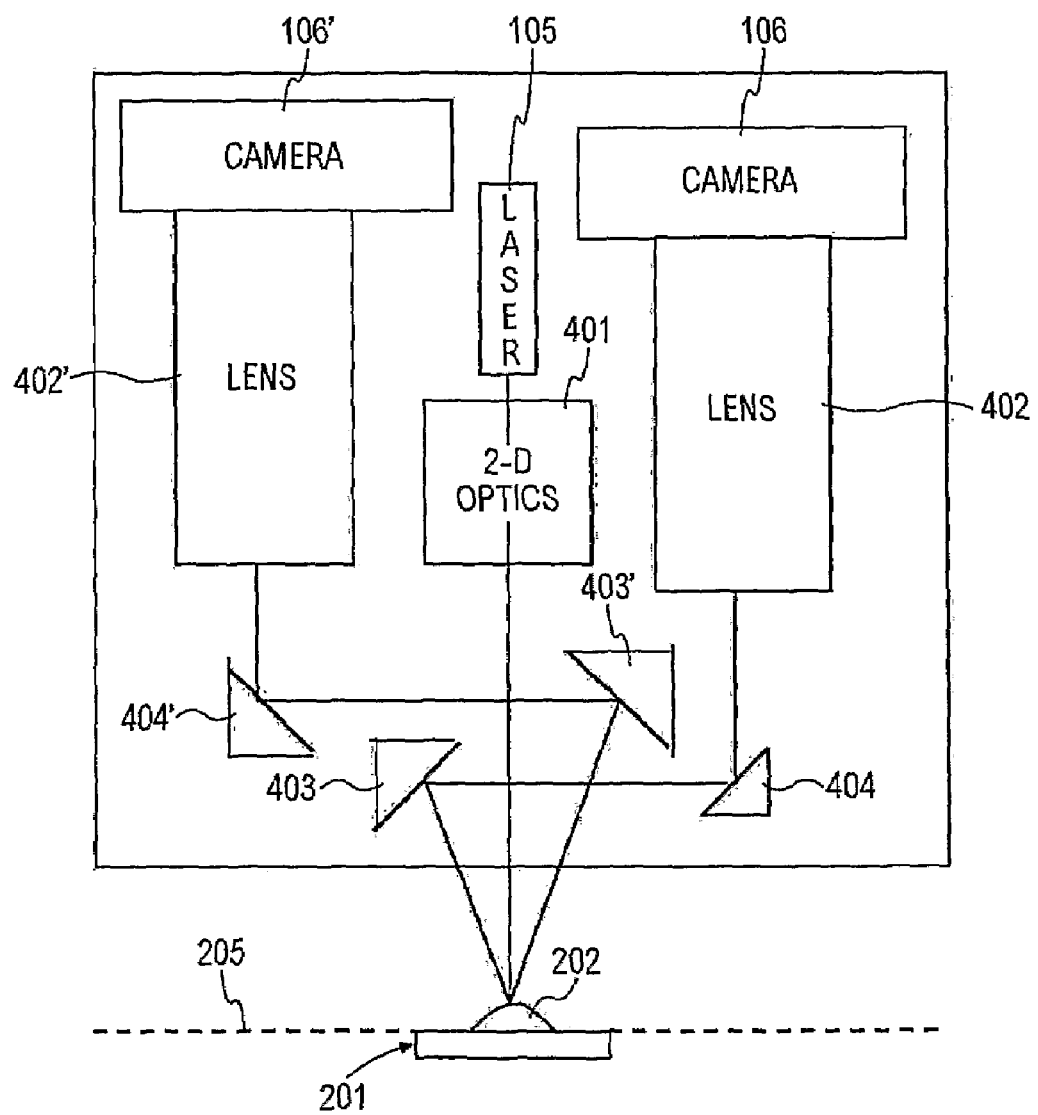
FIG. 7 shows another configuration for the 3-D image acquisition assembly that is catered for height and space limitations.

FIG. 7 shows another embodiment that is catered for height and space limitations. In this embodiment, mirrors are used to fold the optical path to reduce the physical height to cater for the situation of limited height. A pair of mirrors 403 and 404 is provided for directing the reflected light from the device 201 onto the camera 106. Another pair of mirrors 403' and 404' are provided for directing reflected light from the device 201 onto the 106'.

Figure 8:
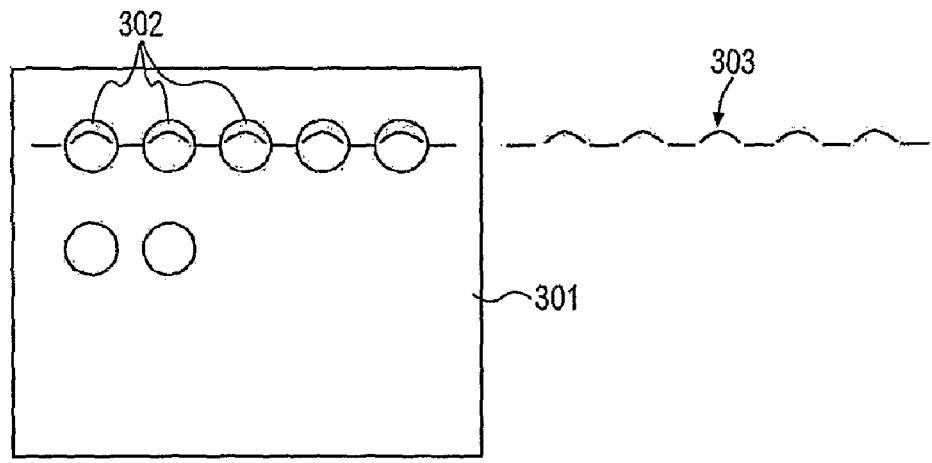
FIG. 8 shows a top view of a ball grid array (BGA) device and a 3-D image of a laser line on a row of solder balls.

FIG. 8 shows a typical ball grid array (BGA) device comprising a planar substrate 301 and an array of solder ball leads 302. Only a representative number of leads are shown for the sake of clarity. The solder balls are reflowed onto pads (not shown), which are connected to conductors of an IC device. It is important, when inspecting the solder ball leads, to verify their proper positions with respect to each other and to the substrate. It is also important to verify the presence of all leads and the co-planarity of the leads. When the 3-D light source 105 illuminates the BGA device, the row of solder ball leads as viewed by the 3-D camera 106 is shown in FIG. 8 as image 303. The 3-D image acquisition assembly 104 continues to capture images at the interval distance between movements; a series of images similar to 303 are formed and processed to extract the profile of the balls and thus enable the system to compute the height of the balls.

Figure 9:
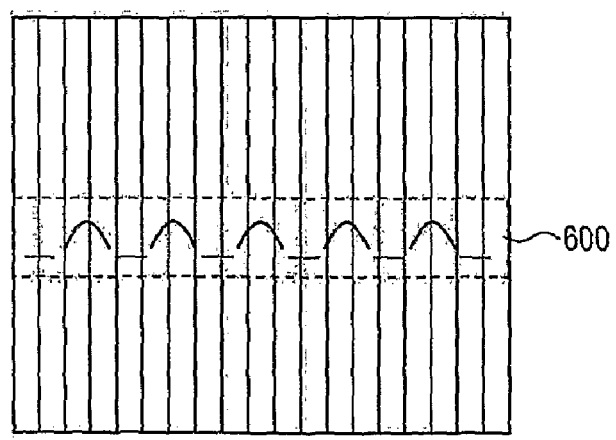
FIG. 9 shows a CMOS image sensor with programmable window size for use in the inspection system to increase the frame rate of image.

FIG. 9 shows a CMOS image sensor with a programmable window size. The image frames rate can be higher when it works with smaller sensor area. The system algorithm allows the smaller window area of interest within the image sensor window size for measuring height and increasing the inspection profiling speed. The frame rate can reach as high as 500 frames per second at full resolution of 1280 (Horizontal) by 1024 (Vertical)—a rate that CCD camera cannot achieve. The programmable window's size feature allows it run even faster at small windows. An inspection speed of 6400 profiles per second can be achieved in our invention when 80 rows of sensor area are used.

Based on the arrangement of the present invention, the 2-D inspection and 3-D inspection can be done while the device 201 is held in the same location along the X direction. Furthermore, the 2-D and 3-D image acquisition assemblies are operable independently of each other. This means that the 2-D image acquisition assembly is not activated when only 3-D inspection capability is required.

It will be appreciated that although several preferred embodiment have been described in detail, various other modifications and improvements can be made by a person skilled in the art without departing from the scope of the present invention.

The invention claimed is:

1. An inspection system for inspecting an electronic devices said system comprising:
   means for holding an electronic device in an inspection plane;
   a 2-dimensional (2-D) inspection assembly comprising:
      a first light source for illuminating the electronic device, wherein the first light source is disposed at a predetermined level above the inspection plane;
      a first optical device configured to reflect the light reflected from the electronic device due to the illumination of the first light source, wherein the first optical device is disposed at a predetermined level above the first light source; and
      a first sensor for capturing the 2-D image of the electronic device by obtaining the light reflected from the first optical device, wherein the first sensor is disposed at a predetermined level above the inspection plane; and
   a 3-dimensional (3-D) inspection assembly comprising:
      a second light source capable of generating a sheet of light onto the electronic device, wherein the second light source is disposed above the first optical device that allows the sheet of light to be transmitted to the electronic device, wherein the second light source is oriented so that the sheet of light is substantially perpendicular to the inspection plane; and
      at least one second sensor for capturing a 3-D profile of the electronic device by obtaining the sheet of light reflected from the electronic device, wherein the second sensor is disposed at a predetermined level above the inspection plane;
   wherein the 2-D inspection assembly and the 3-D inspection assembly can be operated simultaneously.

2. The inspection system of claim 1, wherein the 2-D inspection assembly further comprises a second optical device configured to reflect the light from the first optical device to the first sensor.

3. The inspection system of claim 1, wherein the first optical device can be a beam splitter.

4. The inspection system of claim 2, wherein the second optical device can be a mirror.

5. The inspection system of claim 1, wherein the 3-D inspection assembly comprises two second sensors disposed at a predetermined level above the inspection plane, wherein the two second sensors are symmetrically arranged with the sheet of light in the middle of both second sensors.

6. The inspection system of claim 1, wherein the at least one second sensor is oriented at an acute angle relative to the inspection plane.

7. The inspection system of claim 5, wherein the two second sensors are oriented at an acute angle relative to the inspection plane.

8. The inspection system of claim 1, wherein the at least one second sensor comprises a CCD camera or a CMOS camera.

9. The inspection system of claim 5, wherein the each of the two second sensors comprises a, CCD camera or a CMOS camera.

10. The inspection system of claim 1, wherein the first sensor comprises a CCD camera or a CMOS camera.

11. The inspection system of claim 1, wherein the first light source comprises a ring-shaped LED array.

12. The inspection system of claim 1, wherein the 2-D inspection assembly and the at least one second light source are coaxially aligned.

* * * * *

UNITED STATES PATENT AND TRADEMARK OFFICE
CERTIFICATE OF CORRECTION

PATENT NO. : 7,573,569 B2 Page 1 of 1
APPLICATION NO. : 11/573344
DATED : August 11, 2009
INVENTOR(S) : Yong Joo Puah et al.

It is certified that error appears in the above-identified patent and that said Letters Patent is hereby corrected as shown below:

Column 5, line 32, delete "devices" and replace with "device,"

Signed and Sealed this

Twenty-ninth Day of September, 2009

David J. Kappos
*Director of the United States Patent and Trademark Office*